(12) United States Patent
Langer et al.

(10) Patent No.: US 7,972,576 B2
(45) Date of Patent: Jul. 5, 2011

(54) COILED CAPILLARY FOR COMPENSATING MECHANICAL STRESS

(75) Inventors: Sven Langer, Waldbronn (DE); Manfred Berndt, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 144 days.

(21) Appl. No.: 12/388,918

(22) Filed: Feb. 19, 2009

(65) Prior Publication Data

US 2010/0206044 A1  Aug. 19, 2010

(51) Int. Cl.
*B01L 3/00* (2006.01)
(52) U.S. Cl. .......................... 422/501; 422/507
(58) Field of Classification Search .................. 422/100, 422/501, 507
See application file for complete search history.

(56) References Cited

U.S. PATENT DOCUMENTS

| 5,083,470 | A | * | 1/1992 | Davis et al. ................. 73/864.24 |
| 5,156,809 | A | * | 10/1992 | Hupe et al. ...................... 422/64 |
| 5,164,318 | A | * | 11/1992 | Sato et al. ................... 435/286.4 |
| 5,169,511 | A | * | 12/1992 | Allington et al. .............. 204/451 |
| 5,229,074 | A | * | 7/1993 | Heath et al. ...................... 422/64 |
| 5,334,349 | A | * | 8/1994 | Kelln et al. ...................... 422/63 |

FOREIGN PATENT DOCUMENTS

JP  2004085499  3/2004

* cited by examiner

*Primary Examiner* — Lore Jarrett (57) ABSTRACT

A fluidic device comprising a capillary for conducting a fluid and a pivot arm configured for being pivoted, wherein the pivot arm supports at least a portion of the capillary, and a part of the capillary is coiled to at least partially compensate stress resulting from pivoting of the pivot arm.

20 Claims, 11 Drawing Sheets

COILED CAPILLARY FOR COMPENSATING MECHANICAL STRESS

BACKGROUND

The present invention relates to a fluidic device.

In liquid chromatography, a fluidic sample and an eluent (liquid mobile phase) may be pumped through conduits and a column in which separation of sample components takes place. In a sample loop, the sample may be injected into a fluidic path by a mechanically drivable needle. The drivable needle is controllable to be moved out of a seat of the sample loop into a vial to receive a fluid and back from the vial into the seat. The column may comprise a material which is capable of separating different components of the fluidic analyte. Such a material, so-called beads which may comprise silica gel, may be filled into a column tube which may be connected downstream to other components, such as a detector, a fractioner, a waste, etc., by conduits.

JP 2004085499 discloses an autosampler for a liquid chromatograph which is capable of suppressing a dead volume to the minimum and in which fatigue failure will not occur in a sample loop. The sample loop is fixed in the vicinity of a channel change-over valve and connected to an injection port. A fixing part is rectangular in shape, and the sample loop is fixed, in such a way that the longitudinal direction of the fixing part becomes horizontal. A needle for injection is arranged at a location farthest from the injection port to regulate the length of the sample loop so that the curvature of the sample loop becomes smooth, and is fixed to a needle support part for injection by a fixing part. The fixing part is also rectangular in shape, and the sample loop is fixed, in such a way that the longitudinal direction of the fixing part becomes the horizontal direction.

However, proper operation of movable parts in a sample separation device in combination with a reliable supply of fluid through a capillary may be difficult.

SUMMARY

It is an object of the invention to provide an efficiently operating movable capillary system. The object is solved by the independent claims. Further embodiments are shown by the dependent claims.

According to an exemplary embodiment of the present invention, a fluidic device (such as a liquid chromatography device) is provided which comprises a capillary (such as a tube enclosing a lumen configured as a fluid conduit) for conducting a fluid and a pivot arm (such as a robot arm or robot head capable of being rotated for guiding the pivot arm towards a destination, for instance towards a vial containing a fluid to be injected into the capillary or being adapted for receiving fluid from the capillary) configured for being pivoted, wherein the pivot arm supports at least a portion of the capillary (for instance, a capillary section may be mechanically coupled to a certain extent with the pivot arm so that the pivot arm may transport the capillary to a destination so that the capillary can be brought in fluid communication with another component such as a vial containing a fluid; such a "support" may denote a flexible mounting or loose coupling of a part of the capillary by the pivot arm; for instance, the capillary may be placed in or inserted in the pivot arm or in a supporting section thereof), and a part of the capillary is coiled (for instance the capillary comprises a wound, spiral or helical section which may serve as a coil spring for absorbing or buffering a pivoting force or energy so as to protect other portions of the capillary against an undesired impact by such a pivoting force) to at least partially compensate stress (which may act on the capillary) resulting from pivoting of the pivot arm.

According to another exemplary embodiment, a method of operating a fluidic device is provided, the method comprising conducting a fluid through a capillary, pivoting a pivot arm, and supporting at least a portion of the capillary by the pivot arm, wherein a part of the capillary is coiled to at least partially compensate stress resulting from pivoting of the pivot arm.

According to an exemplary embodiment, a capillary may be mounted to be movable on, with or by a pivot arm in such a manner that pivoting the pivot arm together with a portion of the capillary transports the capillary to a certain destination, for instance to bring the capillary in fluid communication with a fluid container at such a destination. Particularly in a scenario in which such a pivoting has to be performed in a very fast manner (as required, for instance, for high throughput applications) and when the pressure within a lumen of the capillary conducting a fluid is at a high value, the mechanical load and stress acting on the capillary during the pivoting may be very high as well. A corresponding challenge may be particularly pronounced when portions of the capillary shall be moved and other portions of the capillary are to be maintained basically immovable or shall be moved to a smaller extent. According to an exemplary embodiment, a corresponding mechanical stress exerted on the capillary may be significantly reduced by coiling a portion of the capillary selectively in a section of the capillary supported by the pivot arm so that stress resulting from pivoting the pivot arm together with the capillary portion may be buffered or reduced by the coil spring. Consequently, pivoting energy may be partially absorbed or stored by the capillary, thereby protecting the capillary (particularly non-coiled portions thereof) efficiently against damage due to fast and powerful pivoting even when a high pressure is present in a lumen within the capillary.

Next, further exemplary embodiments of the fluidic device will be explained. However, these embodiments also apply to the method.

The capillary may have a needle (or tip) which may have an opening in an end portion thereof and which may be configured for selectively receiving (for instance take up or suck in) fluid from or dispensing (for instance eject) fluid to a fluid container containing the fluid. For example, the pivot arm may control the capillary to approach the needle towards one or more vials (i.e. fluid containers) of an arrangement of vials (for instance a well plate) in order to deposit a fluid in a dedicated one of these vials or to take up fluid from one of these vials. For this purpose, a needle which may for instance be made of a metallic material may be arranged in an end portion of the capillary which can dip or immerse into such a fluid container.

The capillary may have a needle for selectively engaging or disengaging a correspondingly configured seat for dispensing fluid from the capillary into a fluidic conduit in fluid communication with the seat. For example, the above-mentioned needle or another needle may be adapted for being receivable in a seat (for instance of a sample loop of a liquid chromatography apparatus) or to be selectively driven out of this seat for receiving a fluidic sample to be injected into the capillary via the needle. After such an injection procedure which may be performed by a negative pressure in a lumen of the needle, the needle may be driven back into the seat so that the received fluidic sample may then be supplied from the sample loop towards other components of a liquid chromatography device, particularly towards a chromatographic separation column. In such an embodiment, the fluidic device may for instance form part of an autosampler for such a liquid chromatography apparatus.

In an embodiment, the capillary and the needle may be integrally formed. In other words, capillary and needle may be made from one material or as a common component, particularly as a single piece. In such an embodiment, the capillary-needle configuration may be particularly sealed for an application in which a high pressure may be applied to the capillary during ordinary use.

In an embodiment, the coiled part of the capillary may comprise a central portion arranged between two surrounding portions. The central portion may have a number of capillary turns per length which is smaller than a number of capillary turns per capillary length of the surrounding portions. In other words, two tightly wound capillary portion may sandwiched a more loosely wound surrounding portion. The present inventors have recognized that such a configuration with multiple capillary sections having different values of the winding density in a capillary portion assigned to the pivot arm is capable of further reducing stress acting on the capillary during a pivoting motion of the pivot arm.

Another part (i.e. a part differing from the coiled portion) of the capillary carried by the pivot arm may be straight, wherein the straight part may be angularly connected with the coiled part. In such an embodiment, not the whole capillary may be coiled, but the capillary can be formed by a coiled portion and one or more adjacent straight portions. Therefore, a straight portion may be used for instance for bridging relatively large distances between a connected member and the capillary, whereas as the coiled portion may be arranged selectively in such a position at which mechanical stress may act on the capillary during pivoting of the pivot arm. Therefore, different sections of the capillary may be specifically configured in accordance with their desired purpose.

An angle between the straight part and the coiled part may be a right angle (90°). In a surrounding of the pivot arm, insertion of the coiled capillary through the pivot arm may be an advantageous option, particularly in combination with a straight part perpendicular to a coiled part. Such a straight part can then guide the capillary along the pivot arm so that in an end portion of the capillary close to the an end portion of the pivot arm, the capillary may be coupled to a fluid needle via which fluid may be exchanged between capillary and a fluidly coupled member such as a vial.

The capillary may be pressure-resistant. In other words, the capillary may be made from such a material, with a sufficient thickness, etc., that a high pressure does not deteriorate the properties of the capillary regarding mechanical stability and does not result in a fluid leakage out of the capillary. In an embodiment, it may be possible that the capillary is pressure-resistant in the presence of a pressure of at least about 100 bar or more, more particularly of at least about 500 bar, even more particularly of at least about 1000 bar. Therefore, the capillary may be particularly appropriate for HPLC (high performance liquid chromatography) applications in which a high pressure value may occur.

The capillary may comprise a metallic material which may ensure both a stability against high pressure values as well as a sufficient mechanical flexibility, chemical inertness and corrosion resistance. It is also advantageous that such a material is chemically compatible with fluids used in life science apparatuses such as solvents and samples, for instance biological and/or chemical samples. Appropriate materials for the capillary are duplex steel, super duplex steel, cobalt nickel alloys, Elgiloy or Phynox. Hence, the capillary may be pressure-resistant (for instance in an interval between 200 bar and 1000 bar or even up to 1200 bar and more), wherein edge oscillations may be suppressed. A capillary made of stainless steel may be capable to withstand a pressure of 2000 bar. A capillary made of duplex steel may even be capable to withstand a pressure of 4000 bar.

According to an exemplary embodiment, the capillary may have a lumen having a diameter of less than about 1 mm, particularly of less than about 0.2 mm. Therefore, the capability may have very small dimensions for transporting very small fluidic volumes. Such advantageous properties may then be combined with the sufficient mechanical flexibility and the stress absorbing properties provided by such coiled capillaries.

It has turned out to be advantageous when the coiled part of the capillary is helically coiled. Such a helical coiling following the shape of a helix may be manufactured with low effort by simply winding a lumen comprising capillary around a cylindrical tube, thereby obtaining a helically coiling. The pitch of such a helical coiling may then allow a user to flexibly adjust the capillary properties to the requirements of a specific application.

A first end portion of the capillary may comprise, may be coupled to or may be in fluid communication with a needle for being dipped into a fluid container. A second (opposing) end portion differing from the first end portion of the capillary may be connectable to or may be in fluid communication with a metering unit. Such a metering unit may be an entity capable of defining a quantity (for instance a volume or a mass) or a flow rate (for instance a volume or a mass per time) of a fluid to be conducted through the capillary in either direction. Between these end portions, the coiled portion may be arranged.

The pivot arm and the capillary may be arranged relative to one another such that pivoting the pivot arm around a pivot axis may result in a twisting of the coiled part of the capillary or may result in an untwisting of the coiled part of the capillary, depending on the motion direction. Hence, a pivoting motion may result in a rotating motion of the coiled part of the capillary during which the spring-like capillary may absorb potential energy. Hence, pivoting may be transformed into a spring tension.

The capillary may be configured for being (elastically, reversibly or temporarily) deformed, upon pivoting of the pivot arm over an entire pivoting angle range, to an extent which is within an elastic deformation range and beyond a plastic deformation range of the capillary. By correspondingly matching a maximum pivot angle of a robot head with range with an elastic (or Hook-like) deformation characteristic of the spring-like coiled capillary portion may safely prevent the capillary from being destroyed during motion by plastic deformation.

The coiled part of the capillary may be configured to at least partially compensate stress acting on the capillary and resulting from a pivoting of the pivot arm together with the capillary. In contrast to this, a non-coiled capillary may suffer, when being supported on a pivoting pivot arm, from mechanical stress due to bending or folding which may deteriorate the capillary properties and may result in material fatigue. Thus, the coiled portion of the capillary may serve as some kind of buffer for damping forces to prevent damage.

The pivot arm may comprise a pivot hinge around (or about) which the pivot arm is pivotable. Thus, the pivot arm may be mounted so as to be rotatable around a rotation axis which is defined by the orientation of the pivot hinge. The coiled part of the capillary may be arranged or guided along (particularly parallel to) the pivot hinge. By a spatial coincidence between a coiled part of the capillary on the one hand and the pivot hinge on the other hand, a portion of the pivot arm which is not rotated significantly, namely the hinge, can be oriented in close spatial relationship with the coiled capillary portion so as to reduce load acting on the coiled part of the capillary.

According to a particularly advantageous embodiment, the pivot arm may comprise a pivot hinge around which the pivot arm is pivotable, wherein the coiled part of the capillary may be guided through a through hole of or within the pivot hinge. Thus, by guiding the coiled part through a rotation axis of the pivot arm, a space-saving configuration may be achieved together with an arrangement in which the operational demands and the strain and the load acting on the coiled portion of the capillary are maintained sufficiently small, since the hinge axis is a weakly moved portion.

More particularly, the coiled part of the capillary leaving an (or exiting via an) upper end portion of the through hole may be connected to a metering device via an arcuated (or looped) part of the capillary adjacent the upper end portion, and via a sagging part of the capillary adjacent the arcuated part (i.e. the sagging part may be arranged between the arcuated part and the metering device). In other words, under the influence of gravitation, a section of the capillary connecting the metering device with an arcuated part of the capillary may sag freely without impacting a mechanical force on the capillary. The sagging part may therefore have a length which is larger than a shortest path between metering device and arcuated part. Such an excessive length of the capillary in the sagging part may be used advantageously when the rotating motion of the pivot arm (and optionally a superposed additional linear motion) varies (over time) a distance between metering device and needle. The sagging part may then serve as a reserve of capillary length. Additionally, the arcuated part of the capillary may form some kind of loop for connecting the sagging part to the coiled part to thereby ensure a low strain configuration.

The fluidic device may comprise a mechanical guide mechanism configured for mechanically guiding the pivot arm along a straight direction, particularly along a straight guide rail. Therefore, the pivoting motion of the pivot arm may be overlaid or superposed with a for instance linear motion of the pivot arm so that the spatial range of operation of the pivot arm may be increased. For instance, such a one-dimensional motion mechanism in combination with the pivoting or rotation feature may allow the pivot arm in combination with its capillary to serve a large area of fluid containers, for instance for complex autosampler applications.

The fluidic device may additionally comprise a spacing member arranged between the pivot arm and the mechanical guide mechanism for spacing the pivot arm with regard to the mechanical guide mechanism. Therefore, the pivot arm may be spaced by some kind of additional arm so as to prevent undesired abutment of pivot arm against the mechanical guide mechanism.

The fluidic device may further comprise a raise and lowering mechanism configured for selectively raising or lowering (for instance in a vertical direction) the pivot arm, particularly perpendicularly with respect to the linear motion generated by the mechanical guide mechanism. The combination of a pivoting arm with a linear guide mechanism and a raise and lowering mechanism allows for an efficient coverage of a sufficiently large three-dimensional range which is reachable by the capillary.

In an embodiment, the fluidic device may comprise a sleeve element (such as a tube or cylinder) around which the coiled part of the capillary may be coiled. Such a sleeve may serve as a template around which a capillary may be wound and may simultaneously serve as a mechanical support or carrier element for providing mechanical support to the coiled capillary portion.

The fluidic device may further comprise a cantilever along which a straight part of the capillary (which may be coupled next to the coiled part) is guided. Therefore, a member connecting pivot hinge and end portion (or adapter portion for connecting a needle) of the capillary may be realized by the cantilever.

The cantilever and the sleeve may be fastenable to one another and/or to a remainder of the pivot arm, particularly may be fastenable by a bayonet fastener. By taking such a measure it is simplified for a user to assemble or disassemble the configuration in a fast and reversible manner. However, alternative fastening mechanisms (such as a click connection) are possible which allow for a mounting of cantilever and sleeve.

The cantilever and the sleeve may together form a cartridge configuration. Thus, cantilever and sleeve may form an easily substitutable member which allows to insert different geometries, sizes or dimensions within one and the same fluidic device. It is also possible that different capillary diameters or cantilever extensions can be combined.

The pivot arm may be fastenable at the cantilever and at the sleeve. Therefore, all the components may be mounted together to therefore provide for an assembled apparatus.

Therefore, some kind of cartridge may be provided which includes a carrier as well as the capillary and a plastic sleeve around which the coiled portion of the capillary is wound. Such a cartridge may be connected with a sample transport robot arm, for instance may be plugged on such a robot arm. An end portion of the capillary mounted on such a cartridge may then be connected with an immersing needle. Another end portion of the capillary section may be coupled with a metering device.

The fluidic device may further comprise a pump configured for pumping fluid through the capillary. The fluid may be sucked from a vial into the capillary, i.e. may be transported along a first direction to the capillary. It is also possible that the pump is a bidirectional pump which also allows pumping fluid from a metering device through the capillary to be ejected at an end portion of the capillary. As a pump, a piston pump, a peristaltic pump, etc., may be implemented.

The fluidic device may comprise a sample loop for handling a fluidic sample, wherein the capillary may form part of the sample loop. Such a sample loop may be part of a liquid chromatography apparatus and may allow to inject a sample into the sample loop via a needle in an end portion of a capillary which can be pivoted from a seat of the sample loop to immerse into a fluid and, after having taken up the fluid, can be moved back into the seat so that the injected fluid can be introduced via the sample loop onto a chromatographic column for fluid separation. Such a fluid separation may then be performed by separately releasing different fractions of a sample trapped on the chromatographic column by running a gradient during which a solvent with varying composition may be conducted through the chromatographic column.

In an embodiment, the fluidic device may be configured as an autosampler for injecting a fluidic sample in an apparatus being in fluid communication with the capillary. Such an autosampler may be a device or module which, in an automatic manner, allows to handle fluid in a specific manner, for instance in accordance with a dedicated mechanism of controlling different vials so that a specific sample composition may be adjusted.

In an embodiment, the above mentioned apparatus served by the autosampler may be a chromatographic column. Therefore, the autosampler may take up a sample and may inject the sample towards a chromatographic column for sample separation.

The coiled part of the capillary may be mounted in a mechanically biased state (on the fluidic device, particularly on the pivot arm or a supporting part thereof). Particularly, the capillary may be biased by a predefined number of turns (for instance a half turn, a full turn, two turns, etc.). In an embodiment, the coiled capillary (which may have a spiral shape) can be mounted in a biased state. This may allow to obtain a threshold-based mechanical load exerted on the capillary. For instance, by mechanically biasing the coiled part of the capillary by one turn or winding (as compared to a mounting without any tension in the absence of external stress) during assembling capillary and pivot arm and by permanently maintaining such a biasing when no external force appears, the present inventors have successfully run 1 million test cycles without breakage of the capillary.

The fluidic device may thus include or cooperate with a processing element filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 µm to essentially 50 µm. Thus, these beads may be small particles which may be filled inside the separation section of the microfluidic device. The beads may have pores having a size in the range of essentially 0.01 µm to essentially 0.2 µm. The fluidic sample may be passed through the pores, wherein an interaction may occur between the fluidic sample and the pores.

The sample separation device may be configured as a fluid separation system for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the sample separation device may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column (for instance using a gel electrophoresis device or a liquid chromatography device), the different samples may be distinguished, and one sample or band of material may be selectively isolated as a purified sample.

The sample separation device may be configured to analyze at least one physical, chemical and/or biological parameter of at least one component of the mobile phase. The term "physical parameter" may particularly denote a size or a temperature of the fluid. The term "chemical parameter" may particularly denote a concentration of a fraction of the analyte, an affinity parameter, or the like. The term "biological parameter" may particularly denote a concentration of a protein, a gene or the like in a biochemical solution, a biological activity of a component, etc.

The sample separation device may be implemented in different technical environments, like a sensor device, a test device, a device for chemical, biological and/or pharmaceutical analysis, a capillary electrophoresis device, a liquid chromatography device, a gas chromatography device, an electronic measurement device, or a mass spectroscopy device. Particularly, the fluidic device may be a High Performance Liquid device (HPLC) device by which different fractions of an analyte may be separated, examined and analyzed.

The processing element may be a chromatographic column for separating components of the fluidic sample. Therefore, exemplary embodiments may be particularly implemented in the context of a liquid chromatography apparatus.

The sample separation device may be configured to conduct a liquid mobile phase through the processing element and optionally a further processing element. As an alternative to a liquid mobile phase, a gaseous mobile phase or a mobile phase including solid particles may be processed using the fluidic device. Also materials being mixtures of different phases (solid, liquid, gaseous) may be processed using exemplary embodiments. The sample separation device may be configured to conduct the mobile phase through the system with a high pressure, particularly of at least 600 bar, more particularly of at least 1200 bar.

The sample separation device may be configured as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less.

Exemplary embodiments may be implemented in a sample injector module of a liquid chromatography apparatus which sample injector module may take up a sample from a fluid container and may inject such a sample in a conduit for supply to a separation column. During this procedure, the sample may be compressed from, for instance, normal pressure to a higher pressure of, for instance several hundred bars or even 1000 bar and more. An autosampler may automatically inject a sample from the vial into a sample loop. A tip or needle of the autosampler may dip into a fluid container, may suck fluid into the capillary and may then drive back into a seat of a sample loop to then, for instance via a switchable fluidic valve, inject the fluid towards a sample separation section of the liquid chromatography apparatus. The sample in the sample loop may be a steel capillary or the like. However, a mechanical load acting on the needle and the capillary when being moved may be conventionally very high. Such a motion may occur when an autosampler robot moves angularly over a well plate or another arrangement of containers of sample for executing a specific analysis.

Exemplary embodiments intend to connect the sample loop with a pump via a short fluidic path. This may be achieved by guiding the capillary through a robotic axis. To keep the load acting on the capillary as small as possible, the capillary needle may be coiled in a portion at which it is fastened to a pivoting arm so that a pivoting motion results in a coiling or uncoiling of the coiled portion to thereby at least partially compensate forces in an efficient way. To keep fluidic paths short, it may be advantageous to guide the capillary through the pivoting axis of a robot arm. Additionally, it may be advantageous to helically or spirally wind a portion of the capillary needle for compensating pivoting motions of the robot arm.

The capillary may comprise two or more—directly connected or separated—coiled portions which may be coiled with the same pitch or with different pitches. One coiled portion (which may have a high pitch) may be located at a robot hinge of the robot arm. Another coiled portion (which may have a smaller pitch) may be arranged between the robot arm and a metering device for additionally compensating stress.

According to an exemplary embodiment, a very small internal volume of the sample loop may be combined with a large displaceable area or volume of the pivot arm-capillary configuration.

A liquid chromatography system in which a fluidic device according to an exemplary embodiment may be implemented is the Agilent series 1200.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

The illustration in the drawing is schematically.

DETAILED DESCRIPTION

Figure 1:
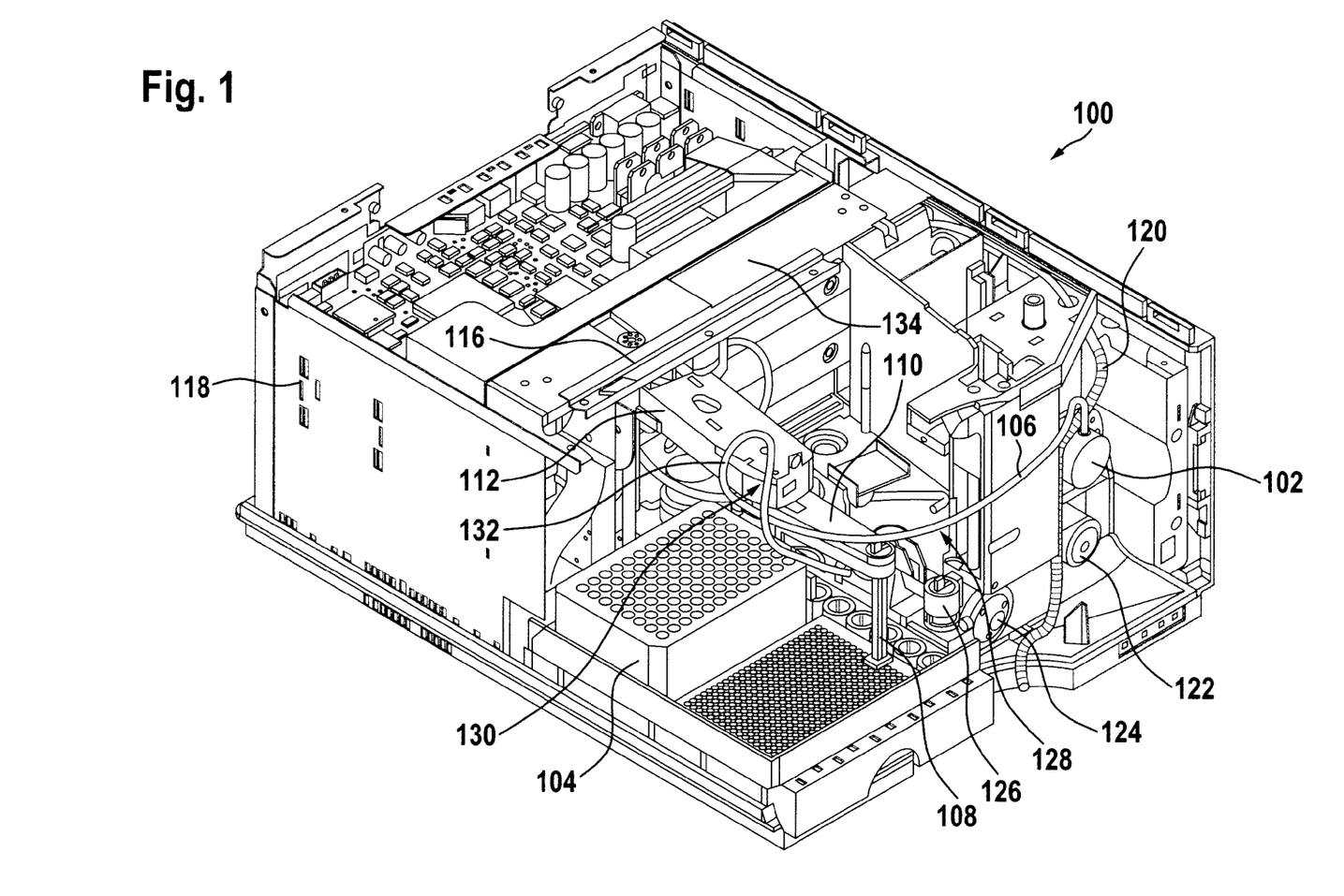
FIG. 1 is a simplified illustration of an autosampler of a liquid chromatography apparatus according to an exemplary embodiment.

FIG. 1 illustrates an autosampler 100 of a liquid chromatography apparatus according to an exemplary embodiment.

The autosampler 100 serves for supplying samples to be analyzed by the liquid chromatography apparatus, particularly towards a metering head 102. The fluidic samples are contained in small vials (not shown) or in sample containers of a well plate 104. The autosampler 100 injects these samples into capillary 106 for distribution over the system.

Two fluidic interfaces at which capillary 106 is fastened are a needle 108 at one end portion and the metering head 102 at the other end portion of the capillary 106. The arrangement of the capillary 106 (which will be shown and described in more detail below) extends from beneath a pivot arm 110 backwards towards a spacer 112 which may also be denoted as a mounting portion for movably mounting pivot arm 110 on the autosampler 100. From here, capillary 106 is guided through several bendings, and back towards the metering head 102.

Figure 2:
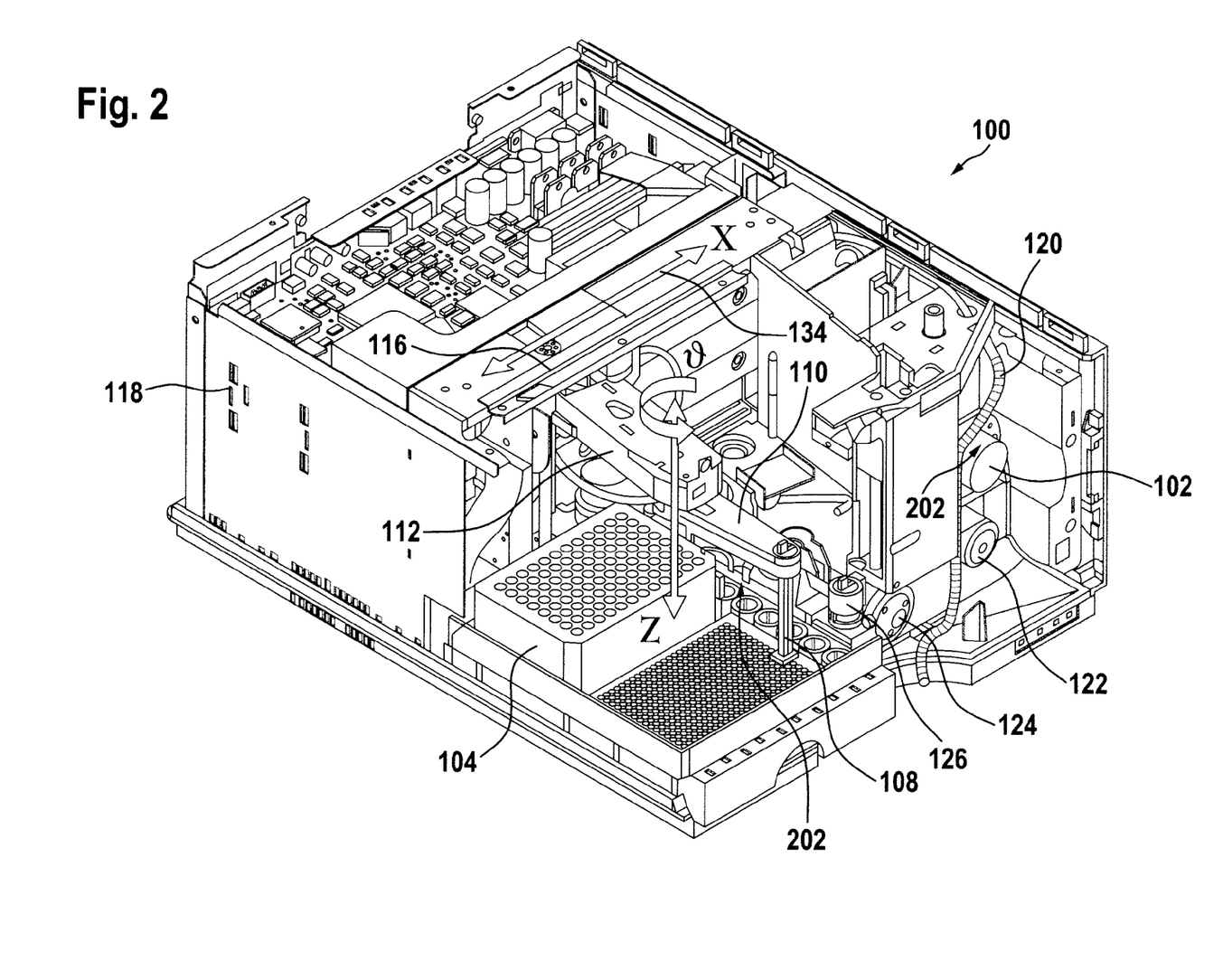
FIG. 2 shows the autosampler of FIG. 1 indicating moving options of components of this apparatus.

Furthermore, FIG. 1 shows an illumination kit 116, a power supply unit 118, loop capillary 120, a peristaltic pump 122, a fluidic switching valve 124 and a needle seat 126. As can be taken from FIG. 1, capillary 106 has a sagging portion 128 for allowing a motion in x-direction (compare FIG. 2). Although not shown in FIG. 1, a section 130 of capillary 106 may be spirally coiled for reducing stress due to a pivoting motion, as will be explained in more detail below referring to FIG. 2. Reference numeral 132 denotes a loop portion of capillary 106.

FIG. 2 again shows most of the components shown in FIG. 1 and additionally defines the x-direction. An x-position can be changed by correspondingly actuating a linear guide mechanism 134. Reference numeral 134 thus refers to a mechanical guide mechanism configured for mechanically guiding the pivot arm 110 along a straight direction, x-direction in FIG. 2, i.e. in a linear manner along a straight guide rail. A z-position can be changed by vertically raising or lowering pivot head 110. Hence, as can be taken from the z-direction in FIG. 2, a raise and lowering mechanism is provided for selectively raising or lowering the pivot head 110. Pivoting pivot head 110 alters theta. Reference numeral 202 denotes fluidic capillary interfaces.

Referring again to FIG. 1, the geometry and the design of the capillary 106 may be selected in such a manner that there is a fluidic path from needle 108 to metering head 102 which is as short or direct as possible in order to keep the flowing resistance and the capillary length as small as possible. Furthermore, the capillary 106 is designed so that the degrees of freedom within the capillary conduit are as large as possible in order to distribute mechanical tensions and stress along the entire length of the capillary 106. Furthermore, accessibility for an exchange of the capillary 106 should be as free as possible.

Figure 3:
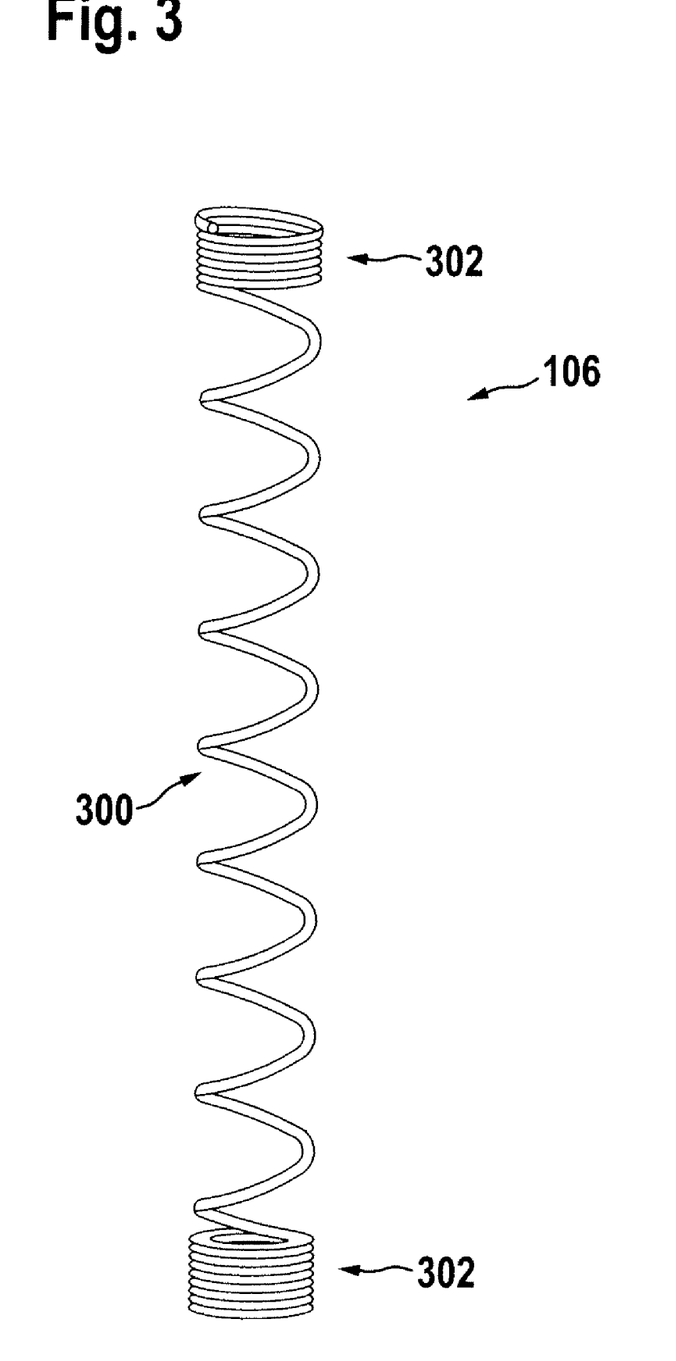
FIG. 3 illustrates a coiled capillary portion of a fluidic device according to an exemplary embodiment.

FIG. 3 shows a detailed view of a part of capillary 106, more precisely of a portion of capillary 106 which portion is guided through the pivot head 110. In other words, FIG. 3 shows a portion of capillary 106 in an environment of the theta axis (compare FIG. 2).

Capillary 106 as shown in FIG. 3 comprises a coiled portion 300 which is guided through a pivot axis of pivot head 110 and is sandwiched symmetrically between two unloaded capillary end portions 302. In other words, during pivoting, stressed region 300 may predominantly receive mechanical load, whereas the capillary ends 302 having a significantly larger pitch (i.e. number of windings per length of the tubular capillary portion shown in FIG. 3) as compared to stressed region 300 remain basically unloaded. Hence, a coiled part of the capillary comprises a central portion 300 arranged between the two surrounding portions 302, the central portion 300 having a number of turns per length with a smaller than a number of turns per length of the surrounding portions 302.

Figure 4:
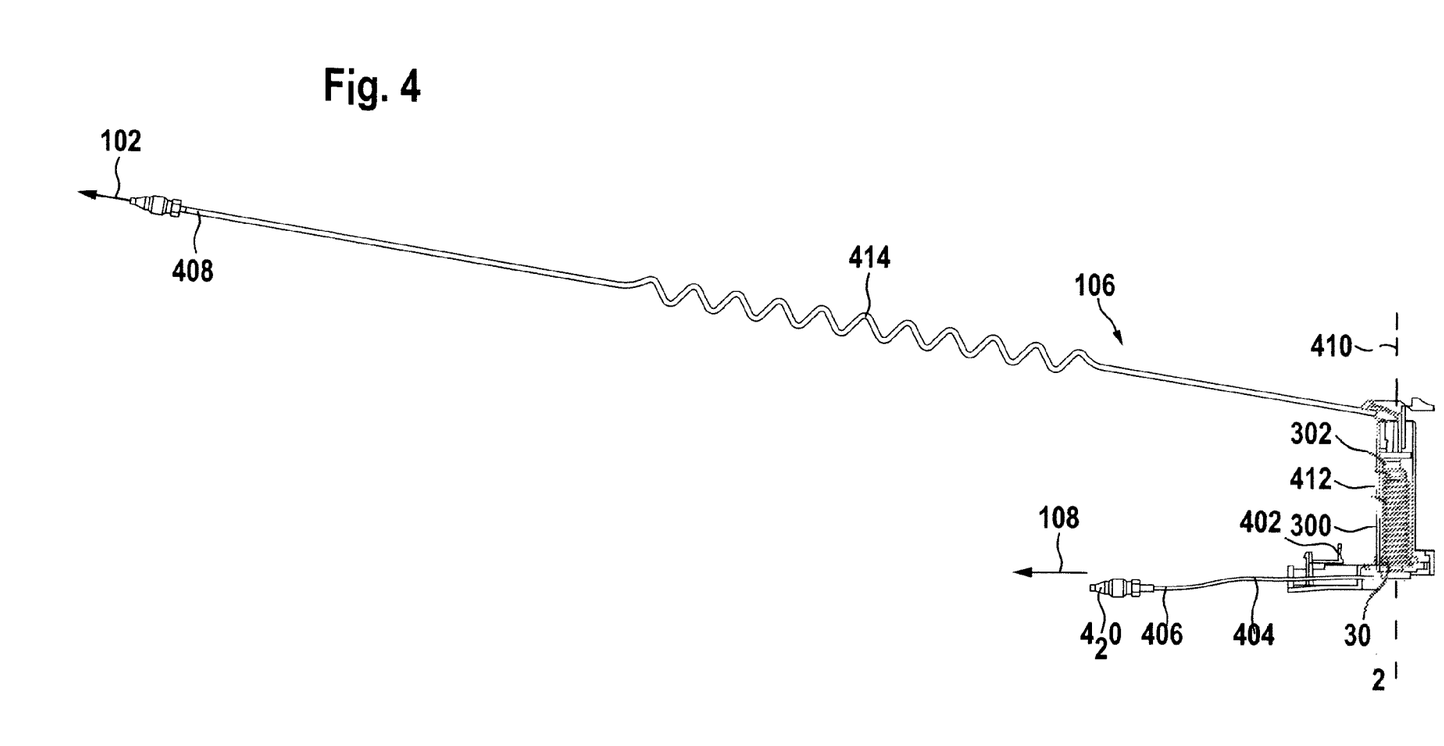
FIG. 4 to FIG. 8 show different views of a cartridge including a capillary according to an exemplary embodiment.

FIG. 4 shows more details regarding the capillary 106.

As already mentioned above, a part 300 of the capillary 106 is coiled to at least partially compensate stress resulting from pivoting pivot arm 110 which is not shown in FIG. 4 but which is to be mounted on a housing 402. Needle 108 to be coupled to fluidic interface 420 is configured for selectively receiving fluid from or dispensing fluid to a fluid container 104 containing the fluid. As can be taken from FIG. 4, a further part 404 of the capillary 106 is basically straight, wherein the basically straight part 404 (aligned horizontally in FIG. 4) encloses a right angle with the coiled part 300, 302 (aligned vertically in FIG. 4).

The capillary 106 is made of super duplex steel and is pressure-resistant for pressures of more than 1000 bar. Therefore, the capillary 106 is capable of withstanding stress of a HPLC experiment. Although not shown in FIG. 4, an inner fluid conducting lumen of capillary 106 has a diameter of about 0.2 mm.

A first end portion 406 of the capillary 106 comprises fluidic interface 420 for connecting the needle 108 for dipping into fluid container 104. A second end portion 408 of capillary 106 is connectable to metering unit 102 (not shown in FIG. 4).

When the housing 402 is mounted on pivot arm 110, the pivot arm 110 and the capillary 106 are arranged relative to one another such that pivoting the pivot arm 110 around a pivot axis (see theta in FIG. 2) results in a twisting or untwisting of the coiled part 300 of the capillary 106. More particularly, the capillary 106 is configured for being deformed, upon pivoting the pivot arm 110 over an entire pivoting angle range, to an extent which is within an elastic deformation range and beyond a plastic deformation range of the material and geometry of the capillary 106 so that the capillary 106 is not damaged during pivoting. Therefore, the coiled part 300 of the capillary 106 is configured to at least partially compensate stress acting on the capillary 106 and resulting from a pivoting of the pivot arm 110 together with the capillary 106.

As can be taken from FIG. 1 and FIG. 4, pivot arm 110 comprises a pivot hinge 410 around which the pivot arm 110 is pivotable, wherein the coiled parts 300, 302 of the capillary 106 are arranged along and accommodated within the pivot hinge 410. For this purpose, the pivot hinge 410 has a through hole extending through the pivot arm 110 through which through hole the coiled parts 300, 302 are guided. This allows for a space-saving configuration and allows further keep stress acting on the coiled parts 300, 302 of the capillary 106 sufficiently small, even when the pivot arm 110 pivots over an entire pivoting angle.

The coiled parts (compare reference numerals 300, 302 in FIG. 3 or FIG. 4) of the capillary 106 leaves an upper end portion of the through hole and is then connected to metering device 102 via an arcuated part 130 of the capillary 106 adjacent the upper portion and a sagging part 128 of the capillary 106 adjacent the arcuated part 130 (compare FIG. 1).

The arrangement of FIG. 4 comprises a sleeve 412 which can be made from a plastic material around which sleeve 412 the coiled parts 300, 302 of the capillary 106 are coiled.

As can be taken from FIG. 4, housing 402 serves as some kind of cantilever along which the straight part 404 of the capillary 106 is guided. The cantilever 402 and the sleeve 412 are fastenable to one another and are shown in FIG. 4 in a fastened state. Cantilever 402 and sleeve 412 together form a cartridge. Pivot arm 110 is fastenable at the cantilever 402 and sleeve 412 configuration.

In order to further compensate stress, another coiled portion 414 is arranged between metering device 102 and cartridge 402, 412 which has a smaller turn number per length as compared to the coiled portion 300.

Figure 5:
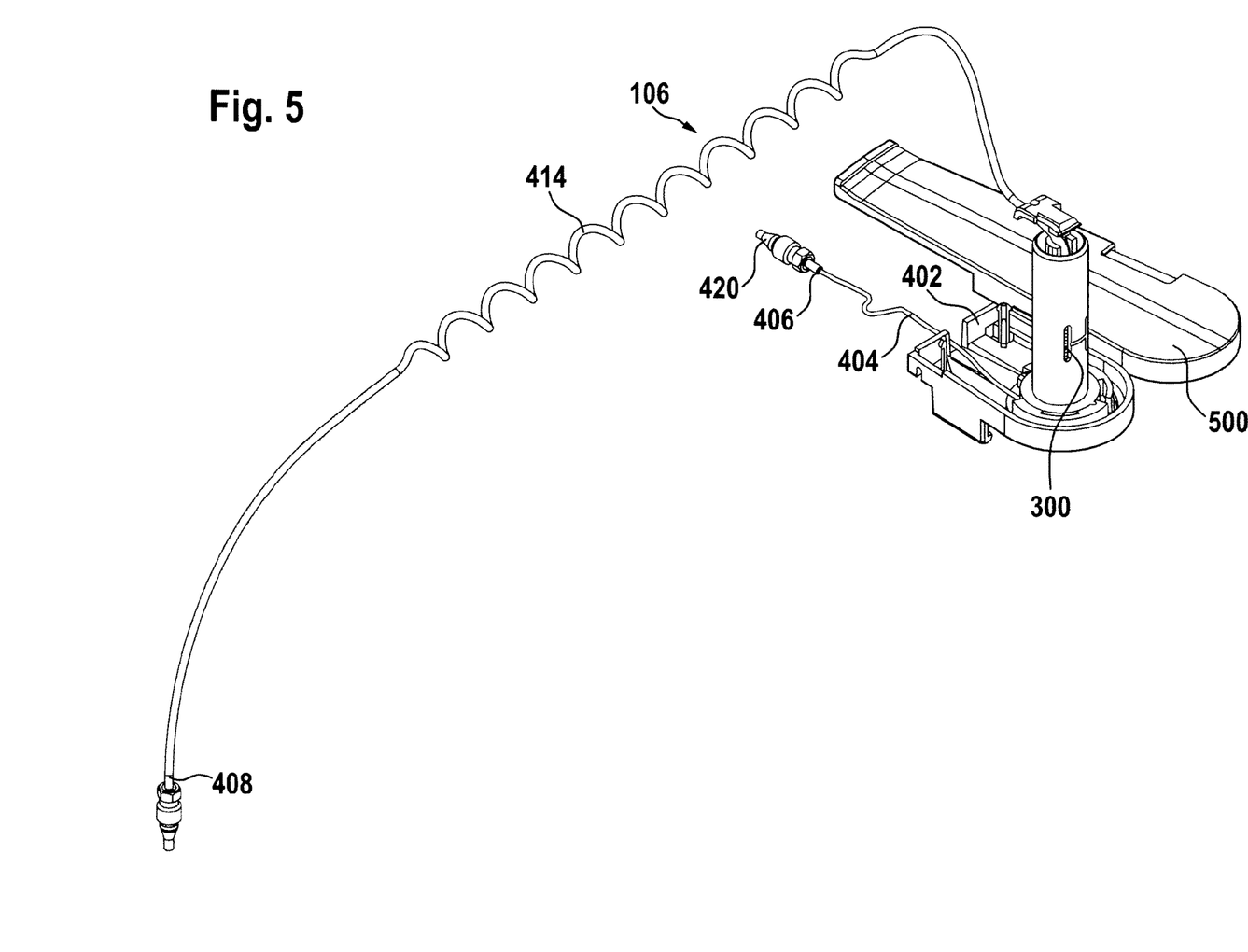

FIG. 5 shows a configuration similar as FIG. 4 when the capillary 106 is partially bent. Such a bending may take place when x and z direction are changed (compare FIG. 2). FIG. 5 shows a further component 500 which can be connected to the cartridge 402, 404.

Figure 6:
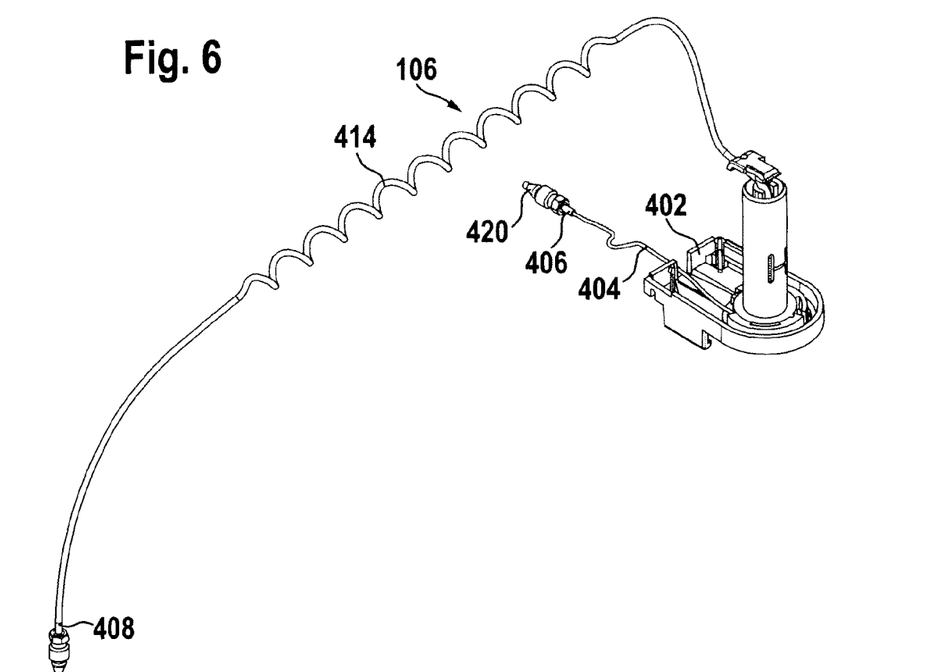
Figure 7:
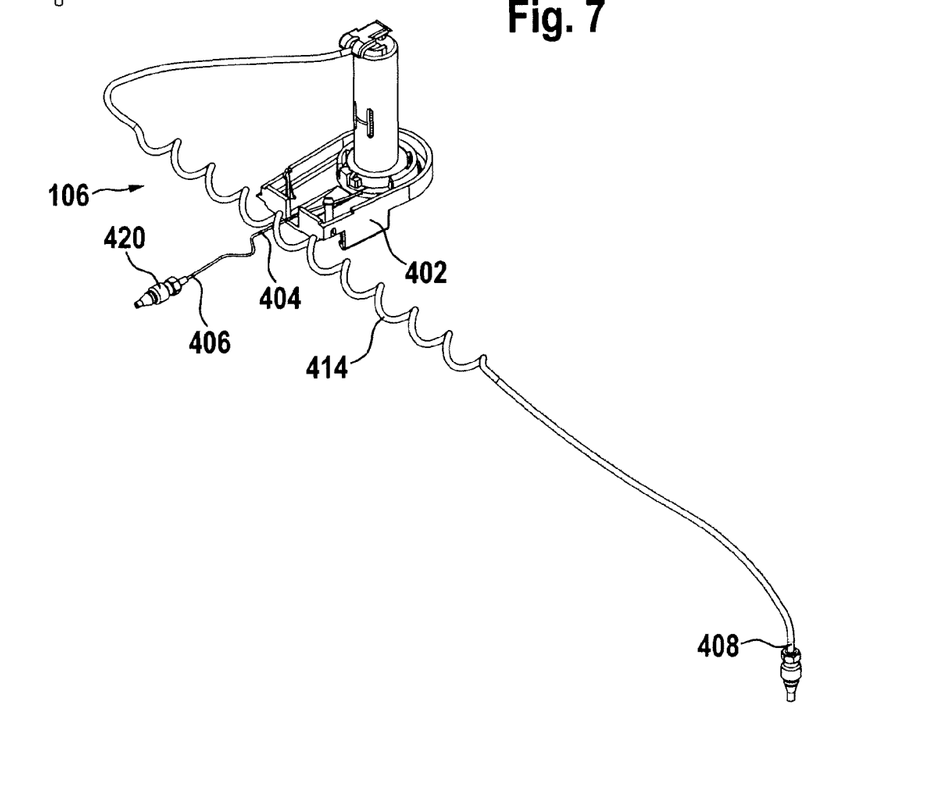
Figure 8:
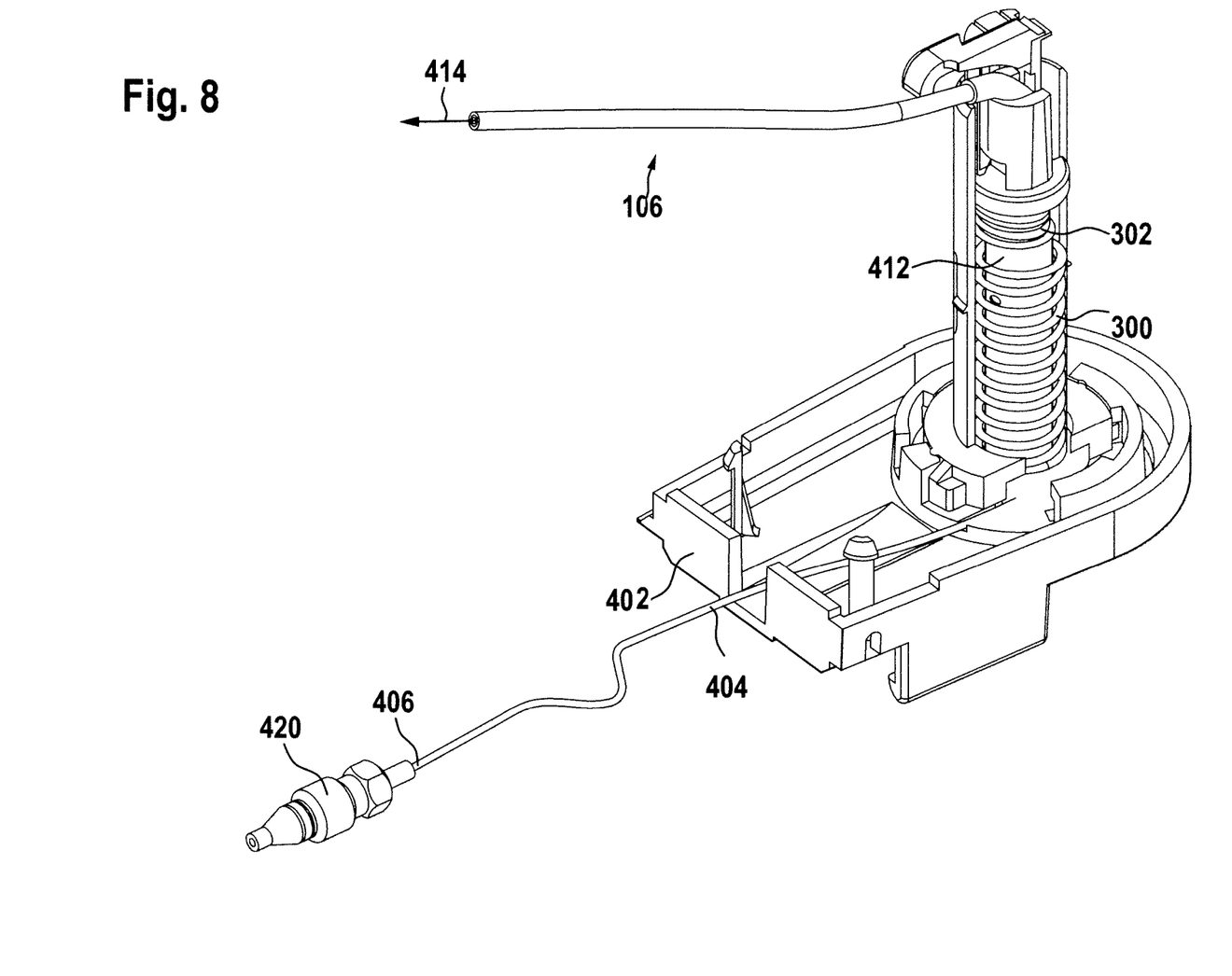

FIG. 6 and FIG. 7 show two further illustrations of the arrangement of FIG. 4 and FIG. 5. FIG. 8 shows a detailed view of a configuration according to FIG. 4 to FIG. 7.

Figure 9:
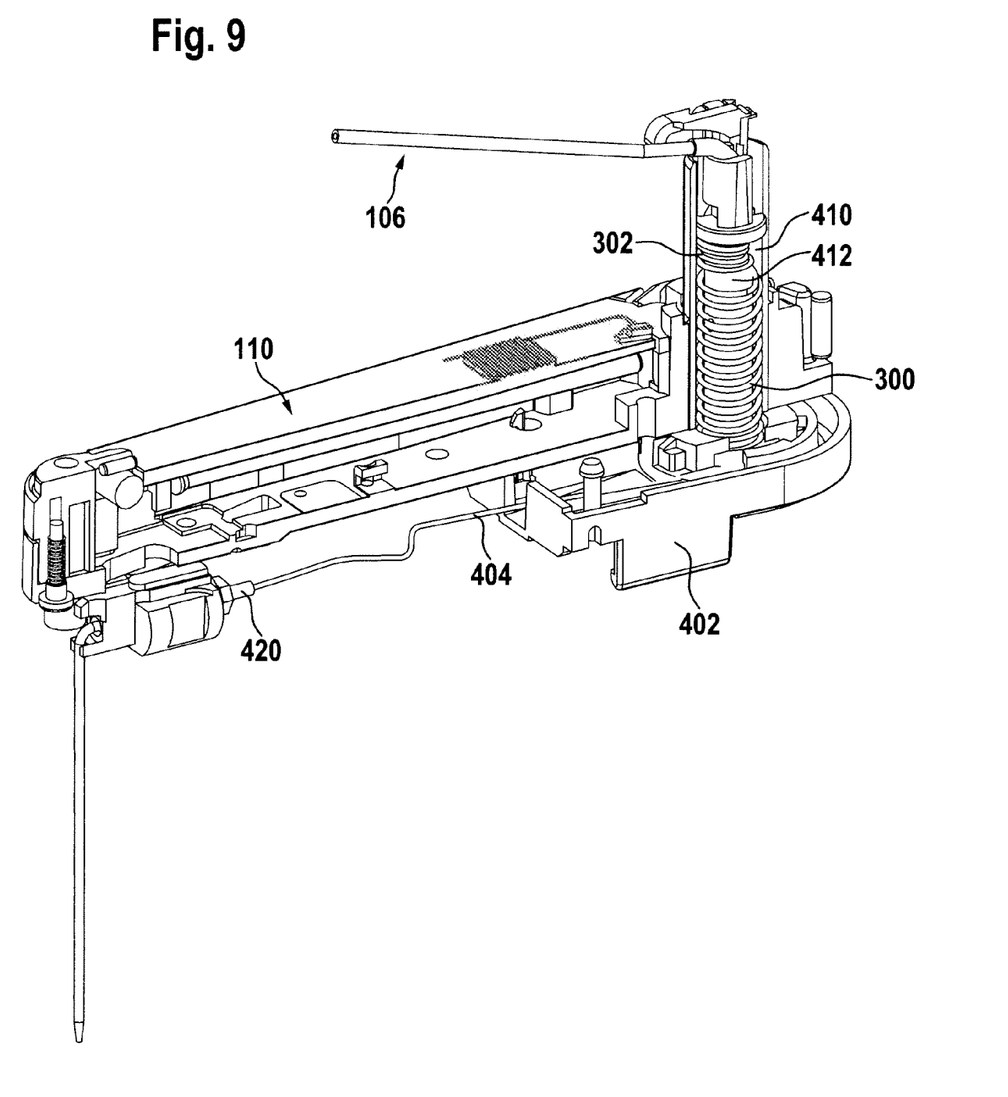
FIG. 9 shows a pivot arm supporting a capillary according to an exemplary embodiment.

FIG. 9 shows an arrangement in which a configuration as shown to FIG. 4 to FIG. 8 is mounted on a pivot head 110. Coupling element 420 shown in FIG. 4 and needle 108 are shown in FIG. 9 as well.

Figure 10:
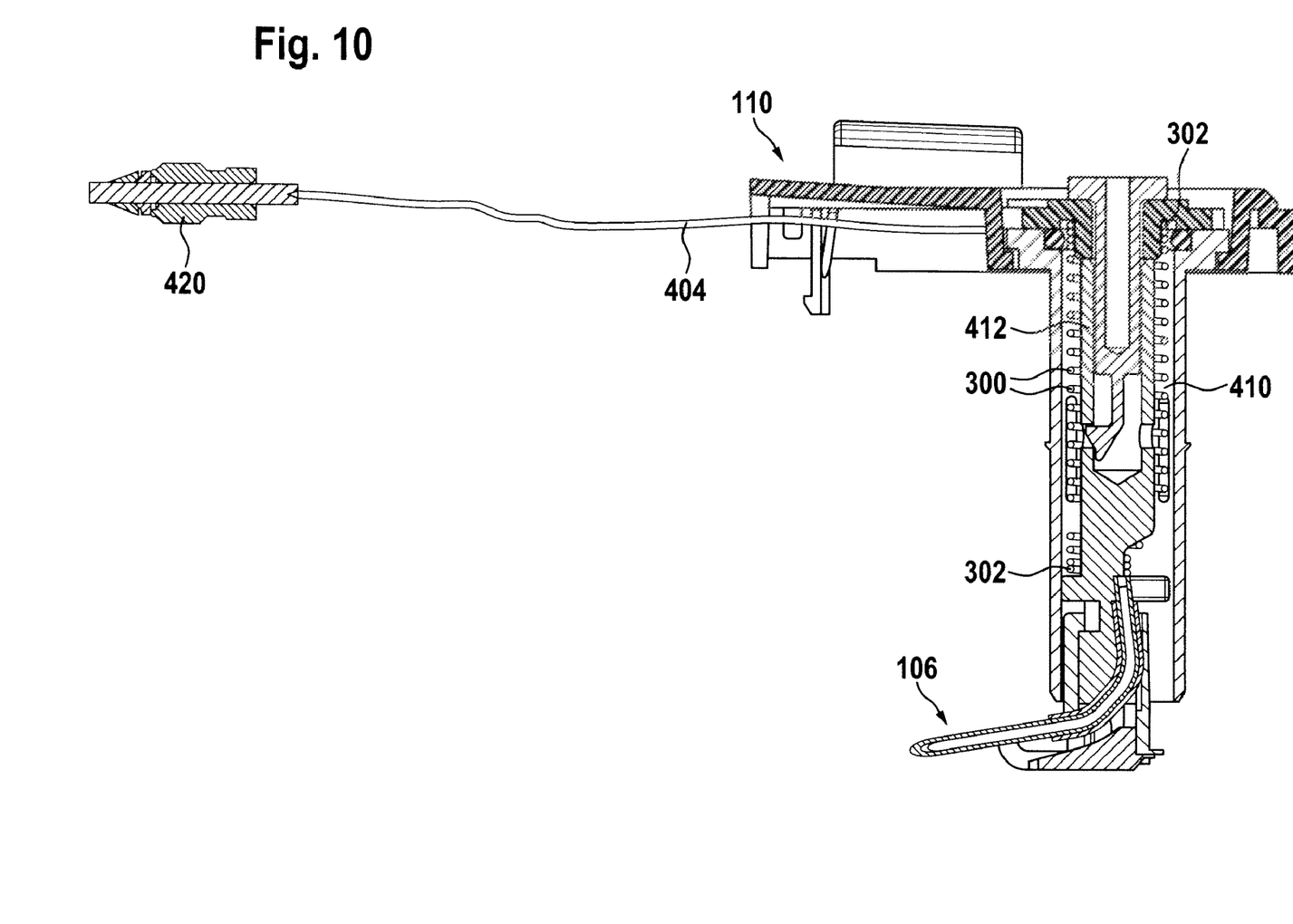
FIG. 10 shows a cross section of a cartridge including a capillary according to an exemplary embodiment.

FIG. 10 shows a cross-sectional view similar to a configuration according to FIG. 4 to FIG. 8.

Figure 11:
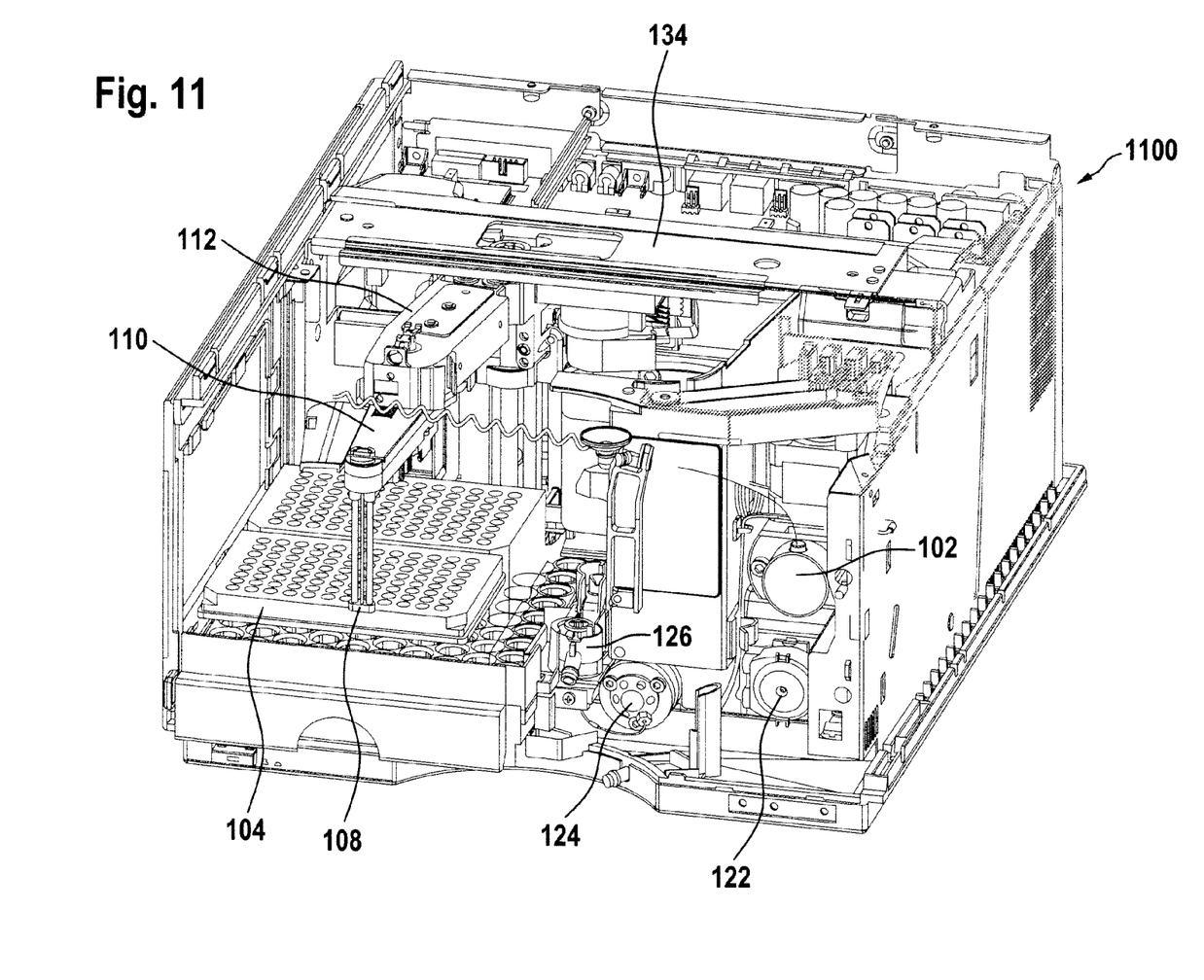
FIG. 11 shows a detailed view of an autosampler of a liquid chromatography system according to an exemplary embodiment.

FIG. 11 shows a three-dimensional view of an autosampler 1100 according to an exemplary embodiment in which a pivot arm 110/capillary 106 configuration as explained above has been integrated.

Figure 12:
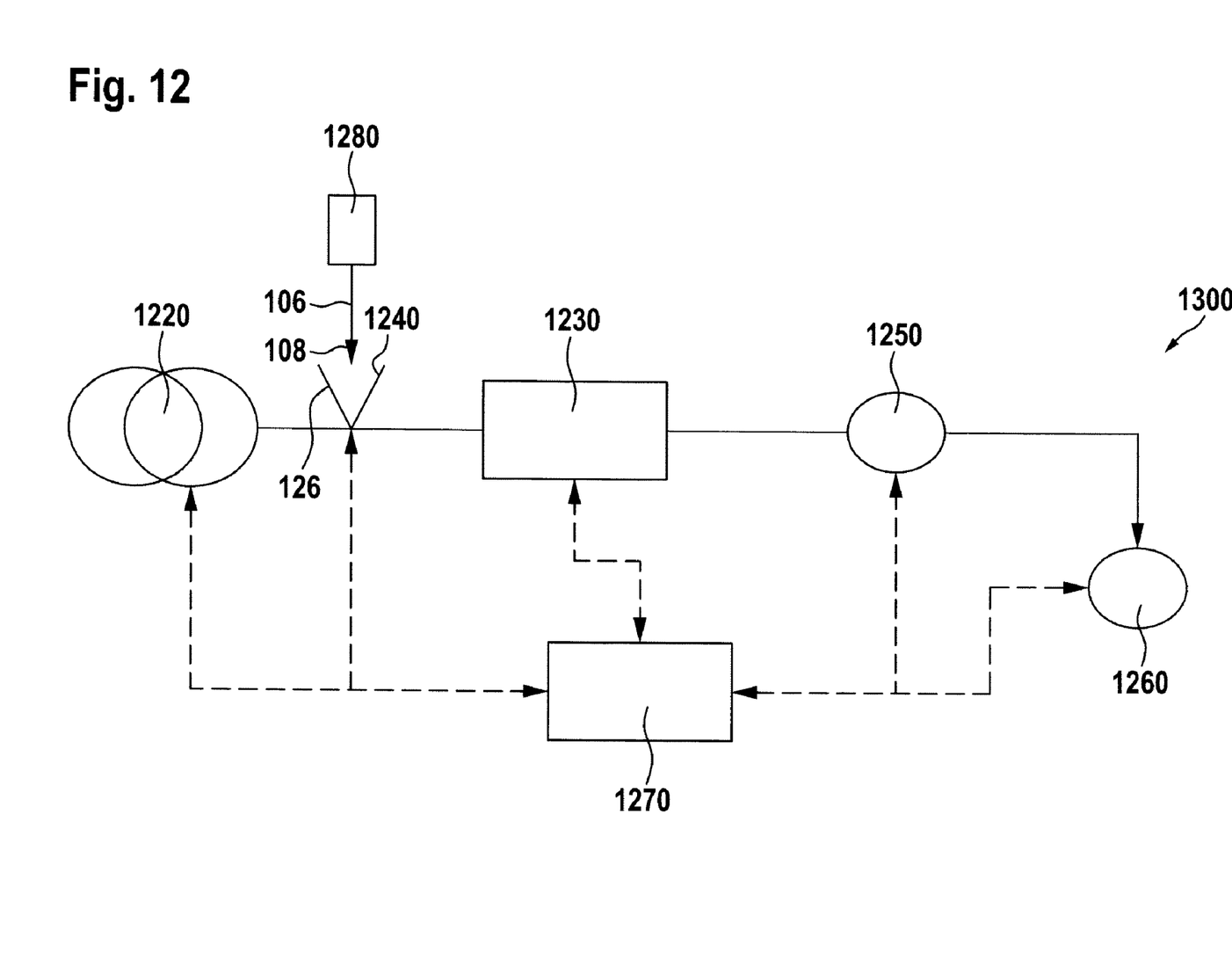
FIG. 12 illustrates a liquid chromatography apparatus according to an exemplary embodiment.

FIG. 12 depicts a general schematic of a liquid separation system 1200. A pump 1220—as a mobile phase drive—drives a mobile phase through a separating device 1230 (such as a chromatographic column) comprising a stationary phase. A sampling unit 1240 can be provided between the pump 1220 and the separating device 1230 in order to introduce a sample fluid to the mobile phase. The stationary phase of the separating device 1230 is configured for separating compounds of the sample liquid. A fluid composition control unit 1270 may be provided for controlling quantities of a fluid introduced into the liquid separation system 1200. A fractionating unit 1260 can be provided for outputting separated compounds of sample fluid. Reference numeral 1250 denotes a detection unit. Further, FIG. 12 schematically illustrates a sample loop 1280 which comprises a pivot arm-capillary configuration as, for instance, described above.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A fluidic device comprising
a capillary for conducting a fluid; and
a pivot arm configured for being pivoted about a pivot axis;
wherein the pivot arm supports at least a portion of the capillary, and a part of the capillary is coiled around the pivot axis to at least partially compensate stress resulting from pivoting of the pivot arm.

2. The fluidic device according to claim 1, wherein the capillary has a needle configured for selectively receiving fluid from or dispensing fluid to a fluid container containing the fluid.

3. The fluidic device according to claim 2, wherein the capillary and the needle are integrally formed.

4. The fluidic device according to claim 1, wherein the capillary has a needle for selectively engaging or disengaging a correspondingly configured seat for dispensing fluid from the capillary into a fluidic conduit in fluid communication with the seat.

5. The fluidic device according to claim 1, wherein the coiled part of the capillary comprises a central portion arranged between two surrounding portions, the central portion having a number of turns per length which is smaller than a number of turns per length of the surrounding portions.

6. The fluidic device according to claim 1, wherein the pivot arm and the capillary are arranged relative to one another such that pivoting the pivot arm around the pivot axis results in a twisting or untwisting of the coiled part of the capillary.

7. The fluidic device according to claim 1, wherein the coiled part of the capillary is configured to at least partially compensate stress acting on the capillary and resulting from a pivoting of the pivot arm together with at least a part of the capillary.

8. The fluidic device according to claim 1, wherein the pivot arm comprises a pivot hinge around which the pivot arm is pivotable, wherein the coiled part of the capillary is arranged along or guided through a through hole of the pivot hinge.

9. The fluidic device according to claim 8, wherein the coiled part of the capillary led through an upper end portion of the through hole is connected to a metering device via an arcuated part of the capillary adjacent the upper end portion and via a sagging part of the capillary adjacent the arcuated part.

10. The fluidic device according to claim 1, further comprising a sleeve disposed along the pivot axis around which the coiled part of the capillary is coiled.

11. The fluidic device according to claim 10, further comprising a cantilever along which a straight part of the capillary is guided.

12. The fluidic device according to claim 11, comprising at least one of the following features:
the cantilever and the sleeve are fastenable to one another;
the cantilever and the sleeve constitute a cartridge; and
the pivot arm is fastenable with the cantilever and the sleeve.

13. The fluidic device according to claim 1, comprising at least one of the following features:
the fluidic device further comprises a pump configured for pumping fluid through the capillary;
the fluidic device further comprises a raise and lowering mechanism configured for selectively raising or lowering the pivot arm;
the fluidic device further comprises a mechanical guide mechanism configured for mechanically guiding the pivot arm along a straight guide rail;
the fluidic device further comprises a mechanical guide mechanism configured for mechanically guiding the pivot arm along a straight guide rail, and a spacing member arranged between the pivot arm and the mechanical guide mechanism for spacing the pivot arm with regard to the mechanical guide mechanism;
the coiled part of the capillary is helically coiled;
the capillary has a lumen having a diameter of less than 1 mm;
the capillary comprises at least one material of the group consisting of a metal, duplex steel, super duplex steel, and a cobalt nickel alloy;
the capillary is pressure-resistant, particularly resistant against a pressure of at least 100 bar;
another part of the capillary carried by the pivot arm is straight, wherein the straight part is angularly connected with the coiled part;
another part of the capillary carried by the pivot arm is straight, wherein the straight part is angularly connected with the coiled part, wherein an angle between the straight part and the coiled part is a right angle;
a first end portion of the capillary comprises a needle for dipping into a fluid container, and a second end portion of the capillary is connectable to a metering unit;
the capillary is configured for being deformed, upon pivoting of the pivot arm over a maximum pivoting angle range, to an extent which is within an elastic deformation range and beyond a plastic deformation range.

14. The fluidic device according to claim 1, wherein the coiled part of the capillary is mounted in a mechanically biased state wherein the coiled part includes a predefined number of turns.

15. The fluidic device according to claim 1, wherein the fluidic device is being configured as an autosampler for injecting a fluidic sample in an apparatus being in fluid communication with the capillary.

16. The fluidic device according to claim 15, wherein the apparatus is a chromatographic column.

17. The fluidic device according to claim 1, comprising at least one of the following features:
the fluidic device comprises a sample loop for handling a fluidic sample, wherein the capillary forms part of the sample loop;
the fluidic device is configured as a sample separation device for separating a fluidic sample;
the fluidic device is configured to analyze at least one physical, chemical and/or biological parameter of at least one compound of a fluidic sample;
the fluidic device comprises at least one of the group consisting of a sensor device, a test device for testing a device under test or a substance, a device for chemical, biological and/or pharmaceutical analysis, a capillary electrophoresis device, a liquid chromatography device, an HPLC device, a gas chromatography device, a gel electrophoresis device, and a mass spectroscopy device;
the fluidic device is configured to conduct the fluid with a high pressure;
the fluidic device is configured to conduct the fluid with a pressure of at least 100 bar
the fluidic device is configured to conduct a liquid fluid;
the fluidic device is configured as a microfluidic device;
the fluidic device is configured as a nanofluidic device.

18. The fluidic device according to claim 1, wherein the fluidic device comprises a processing element for processing a fluidic sample.

19. The fluidic device according to claim 18, comprising at least one of the following features:
the processing element is configured for retaining a part of components of a fluidic sample and for allowing other components of a mobile phase to pass the processing element;
the processing element comprises a separation column;
the processing element comprises a chromatographic column for separating components of a fluidic sample;
at least a part of the processing element is filled with a separating material;
at least a part of the processing element is filled with a separating material, wherein the separating material comprises beads having a size in the range of 1 pm to 50 pm;
at least a part of the processing element is filled with a separating material, wherein the separating material comprises beads having pores having a size in the range of 0.01 pm to 0.2 pm.

20. A method of operating a fluidic device, the method comprising
conducting a fluid through a capillary;
pivoting a pivot arm about a pivot axis; and
supporting at least a portion of the capillary by the pivot arm, wherein a part of the capillary is coiled around the pivot axis to at least partially compensate stress resulting from pivoting of the pivot arm.

* * * * *

UNITED STATES PATENT AND TRADEMARK OFFICE
CERTIFICATE OF CORRECTION

| | | |
|---|---|---|
| PATENT NO. | : 7,972,576 B2 | Page 1 of 1 |
| APPLICATION NO. | : 12/388918 | |
| DATED | : July 5, 2011 | |
| INVENTOR(S) | : Sven Langer et al. | |

It is certified that error appears in the above-identified patent and that said Letters Patent is hereby corrected as shown below:

In column 14, line 28, in Claim 17, delete "bar" and insert -- bar; --, therefor.

In column 14, lines 49-50, in Claim 19, delete "of 1 pm to 50 pm;" and insert -- of 1 µm to 50 µm; --, therefor.

In column 14, line 54, in Claim 19, delete "of 0.01 pm to 0.2 pm." and insert -- of 0.01 µm to 0.2 µm. --, therefor.

Signed and Sealed this
Twentieth Day of September, 2011

David J. Kappos
*Director of the United States Patent and Trademark Office*